United States Patent [19]

Roberts

[11] 4,224,944
[45] Sep. 30, 1980

[54] EPILATION APPARATUS

[76] Inventor: Wallace A. Roberts, 88 N. Main St. Bellingham, Mass 02019

[21] Appl. No.: 935,091

[22] Filed: Aug. 21, 1978

Related U.S. Application Data

[63] Continuation-in-part of Ser. No. 756,897, Jan. 5, 1977, abandoned.

[51] Int. Cl.³ ............................................. A61B 17/41
[52] U.S. Cl. .................................................. 128/303.18
[58] Field of Search ....................... 128/303.18, 303.13, 128/303.14, 303.17, 419 R, 421, 422, 423

[56] References Cited

U.S. PATENT DOCUMENTS

| 2,238,344 | 4/1941 | Schuler et al. | 128/303.18 |
|---|---|---|---|
| 2,700,975 | 2/1955 | Hopfinger et al. | 128/303.18 |
| 3,054,405 | 9/1962 | Tapper | 128/303.18 |
| 3,127,895 | 4/1964 | Kendall et al. | 128/422 |
| 3,315,567 | 4/1967 | Donelson | 128/303.18 |
| 3,359,982 | 12/1967 | Guiorguiev | 128/303.18 |
| 3,478,744 | 11/1969 | Leiteo | 128/303.14 |
| 3,670,737 | 6/1972 | Pearo | 128/422 |
| 3,851,651 | 12/1974 | Icenbice, Jr. | 128/422 |
| 3,999,552 | 5/1975 | Huggins | 128/303.13 |
| 4,155,363 | 5/1979 | Letchworth et al. | 128/303.18 |

Primary Examiner—Lee S. Cohen
Attorney, Agent, or Firm—William Nitkin

[57] ABSTRACT

For the process of epilation by electrocogulation, a solid state circuit for the production of high frequency waves at predetermined timed intervals and intensities, the wave produced having slow rise and decay periods. An integrated circuit charges a timing capacitor which directs an amplification circuit consisting of transistors to direct intermittently timed wave-producing regulated voltage to a probe at the end of a coaxial cable having a predetermined impedance. An overrated transistor in an output circuit feeding the wave producing probe is capable of withstanding reflected and standing waves produced at said probe.

1 Claim, 3 Drawing Figures

EPILATION APPARATUS

BACKGROUND OF THE INVENTION

This Application is a continuation-in-part of my previously filed application for Epilation Apparatus and Method, Ser. No. 756,897, filed 1/5/77, and now abandoned.

The present invention relates to solid state circuitry for an improved epilation apparatus which outputs high frequency waves and more particularly to circuitry which by means of timed integrated circuitry pulses and controls a transistor combination which acts as an amplifier-buffer to transfer and to drive an output stage wave caused to have a gradual surge to and decay from its amplitude.

It is well-known that hair may be permanently removed by destroying the papilla at the base of the hair within the hair follicle. One means of destroying the papilla is electrolysis whereby direct current levels over a relatively long duration are directed to the papilla by means of an appropriate probe needle. This process causes the disassociation of water molecules which constitute a large percentage of the total composition of the papilla. Electrolysis, however, has been disfavored as it is a painful process.

Developments in the field of epilation apparatus have brought about the utilization of high frequency radio waves, directed by an appropriate probe, to cause the vibration of the molecules in the papilla. The vibrating molecules consequently heat and internally destroy the papilla with less discomfort than the standard electrolysis process. This process is known as electro-coagulation. A typical radio frequency epilator has a probe with a needle point or blade length approximately ¼ in. long which is inserted into the follicle usually between ⅛-¼ in. Since it is not desirable to penetrate the wall of the follicle or to puncture a capillary, some needle points are bulbous in shape. This probe is connected by a cable to the unit which produces the radio frequency energy commonly on a frequency of 13.56 megahertz.

The effectiveness of the process and amount of energy necessary to remove the hair depends upon the size of the hair and the moisture gradient of the skin about the hair. Since individual hairs and areas, even upon the same subject, will vary, problems arise in a depilatory system due to reflected waves returning to the system when the needle probe is not matched to the impedance of the skin.

To combat the problem of standing waves, it is presently common within the art to use transmitting tubes rather than solid state circuitry to produce the wave. The embodiments contain a timing stage which consists of a resistor-capacitor circuit and tube. To obtain timing within a range of fifty milliseconds to 0.75 seconds a large value electrolytic capacitor is necessitated. Such capacitors are not inherently stable and are prone to leakage which, with age, will cause timing changes. Further, due to variations in leakage between capacitors, the timing from unit to unit could vary substantially.

Since the timing circuit controls the duration of the output high frequency waves, more reliable components have been desired to control the RF wave propagation.

Although tubes withstand reflective standing waves well, they have well-known attendant disadvantages such as bulk, short life spans and environmental heating. When the tubes heat other components such as the above-mentioned capacitor, it will dry out and further lose efficiency. Also as the tubes age, they become less efficient. Further to achieve precise timing a large value capacitor must be utilized with the tubes.

Although the above-mentioned epilators which produce high frequency waves have reduced the attendant discomfort associated with epilation processes, certain discomfort is present. The application of the output waves produced by these apparatus is in a square wave form having an instantaneous rise to peak amplitude and it has been found that the sudden power surges cause much of the pain.

The present invention is therefore contemplated to combat the aforementioned disadvantages as will become apparent from the following specification.

SUMMARY OF THE INVENTION

It is an object of the present invention to produce an epilation device having a high frequency wave output which gradually surges to a peak amplitude and gradually decays therefrom through the use of solid state circuitry.

It is also an object of the present invention to provide a constantly accurate and precise wave control output timing circuit through the utilization of an integrated circuit which produces a constant current to linearly charge a low value capacitor which acts as a timer control and to combine the same with transistorized amplification-buffer circuitry which controls a regulated oscillating voltage which produces the output wave.

In the present invention an integrated circuit is powered to charge a small value capacitor which has a low leakage potential. A regulated current is oscillated to a combination of amplifying transistors, one of which is directed by the timing circuit to control the regulated current flow to the output. A capacitor to modify the slope of the output wave surge and decay is interposed upon the circuit between the amplifying transistor combination and output stage.

It is therefore an object of the present invention to provide a epilation apparatus which operates at cool temperatures, which is light weight in embodiment, which has long life and which is reliable in operation. The accomplishment of the foregoing objects will become apparent with reference to the following drawings and descriptions thereof.

DESCRIPTION OF THE PREFERRED EMBODIMENT

Figure 1:
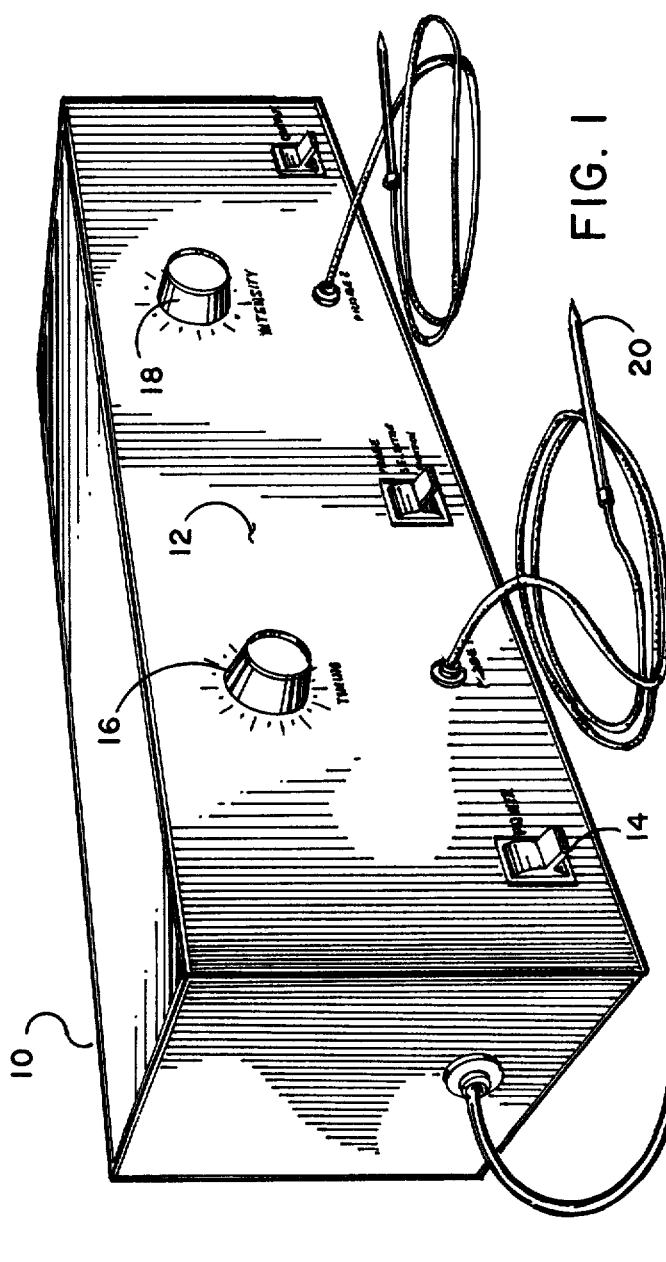
FIG. 1 is a perspective view of the embodiment of an epilator unit of the present invention.

Referring now to the drawings and in particular to FIG. 1, an epilator unit of the present invention is generally designated by reference numeral 10 in the perspective view thereof. Front panel 12 contains manual control apparatus including on-off switch 14 and timing control 16 and intensity control 18. Manual timing control 16 allows the operator to determine and preset the length of time the high frequency waves will be output as directed by a timing circuit. This control will usually scale a range from fifty milliseconds to 0.93 seconds. This intensity control will scale a range of from zero to six watts with five watts being a common intensity utilized. Probe 20, which outputs the high frequency waves, by means of a coaxial cable with a predetermined impedance, is appropriately connected with and locked to a circuit connection on front panel 12. A switch 22, preferably embodied as or activated by a foot pedal, activates the timing circuitry.

Figure 2:
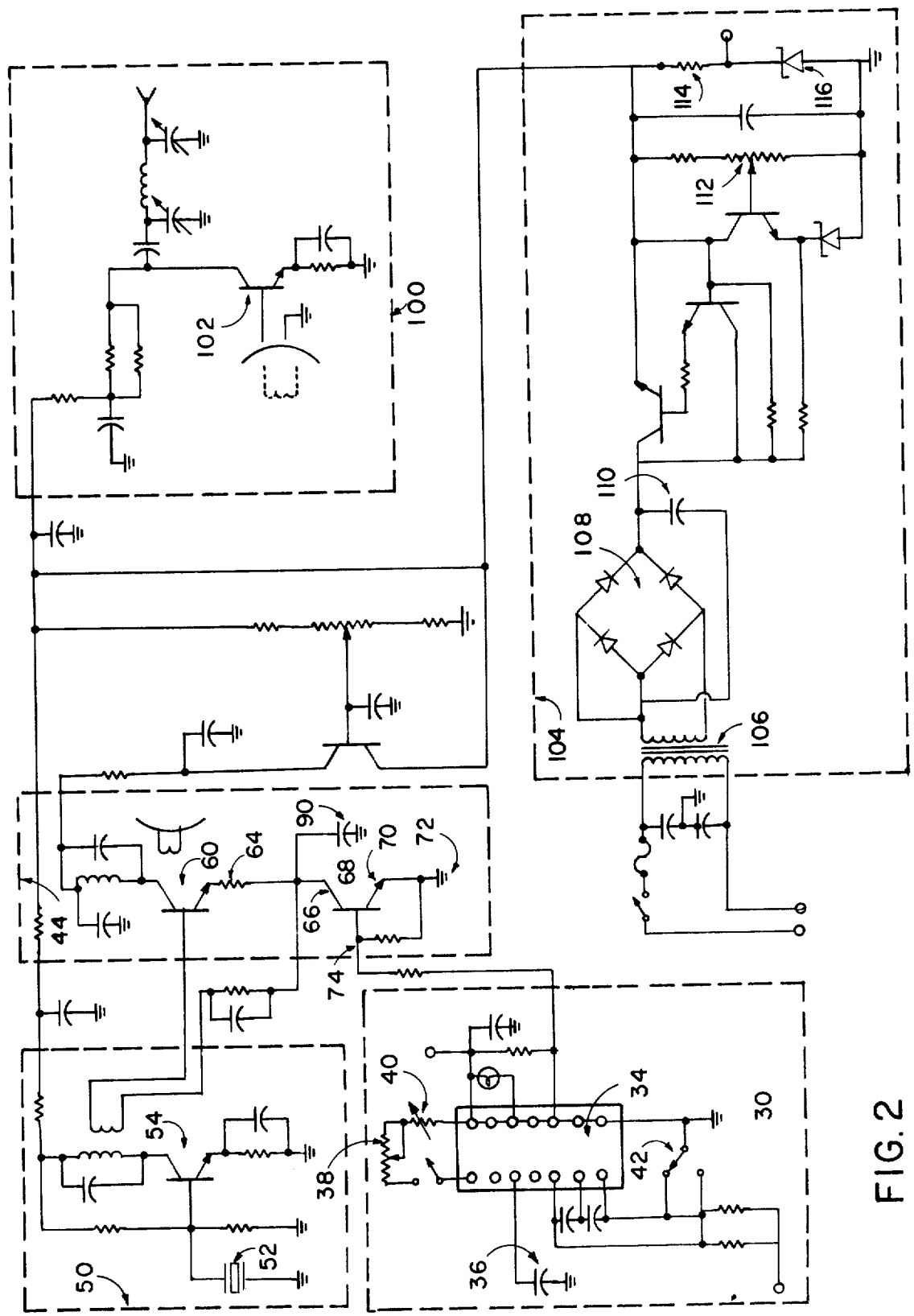
FIG. 2 is a schematic of solid state circuitry to drive a high frequency wave-producing epilator of FIG. 1.

Referring now to FIG. 2 the relevant circuitry of the present invention is illustrated in schematic form with the timing circuitry being generally designated by reference numeral 30. Timing circuit 30 is fed by power supply 104 which may be comprised of a transformer and bridge rectifier. The power produced thereby is filtered by means such as a capacitor and tri-zoned to divide into a regulator circuit to supply eventual output current, preferably thirty-eight volts, and to supply timing circuit actuation current, preferably sixteen volts.

The power supply circuitry 104 can consist of a 50 volt 1 amp transformer 106. The output of the transformer passes into a bridge rectifier circuit 108 and the DC rectified voltage output is filtered by a 2500 microfarad capacitor 110 and then passes into a typical filtering type regulator circuit. The regulation circuit consists of a regulator circuit containing three transistors and one zener diode which makes up the 38 volt supply for the unit and which can be trimmed by trimmer 112. The 38 volts also pass through a 125 ohm resistor 114 and into a 16 volt zener diode 116 which is used to supply the power to the integrated circuit 34 of the timing control within section 30 on the schematic which requires 16 volts.

Timing circuit 30 is comprised primarily of integrated circuit 34 which may be an XR 220 integrated circuit or equivalent. Integrated circuit 34 linearly charges capacitor 36, which controls the actual timing by means of a constant current. Timing control member 16 may be associated with potentiometer 38 to set the timing duration of the output actuation pulses of timing circuit 30. Trimmer potentiometer 40 may be used to initially preset the duration within proper specifications, preferably 50 milliseconds to 0.93 seconds. Foot switch 22 of FIG. 1 has complementary circuit switch 42 which upon closure activates timing circuit 30.

After the desired wave timing has been preset and switch 42 has closed and activated timing circuit 30 to pulse, the pulse proceeds to solid state amplifier circuit, generally designated 44. Amplifier circuit 44 also receives voltage from power supply 104 as acted upon by oscillator circuitry 50. Oscillator circuitry 50 primarily consists of a crystal 52 which operates in conjunction with transistor 54, the output thereof being tuned into amplifier circuit 44. Oscillator crystal 52 is preferably a 13.56 megahertz crystal or equivalent.

Circuit 44 is characterized by transistor 60 which collects oscillating unit power. The emitter 70 of transistor 68 goes to ground 72. Base 74 of transistor 68 receives timed pulses from timing circuit 30 directing it to turn on or off and when turned on, being turned on only as long as the preset time. The only time amplifier circuit 44 will amplify and output to the output probe is when transistor 68 is turned on or in essence shorted out.

In operation, when switch 42 is closed, transistor 68 is pulsed for a predetermined time, that being between the aforesaid timing, turns on and allows conductance of oscillating voltage from transistor 60 to the output stage.

The aforesaid circuitry is capable, provided a proper output stage is associated therewith, of matching prior art performance for the removal of hair. However, with reference to FIG. 3, a square wave 80 is produced as illustrated. Maximum wave amplitude is reached almost immediately due to the surge.

Figure 3:
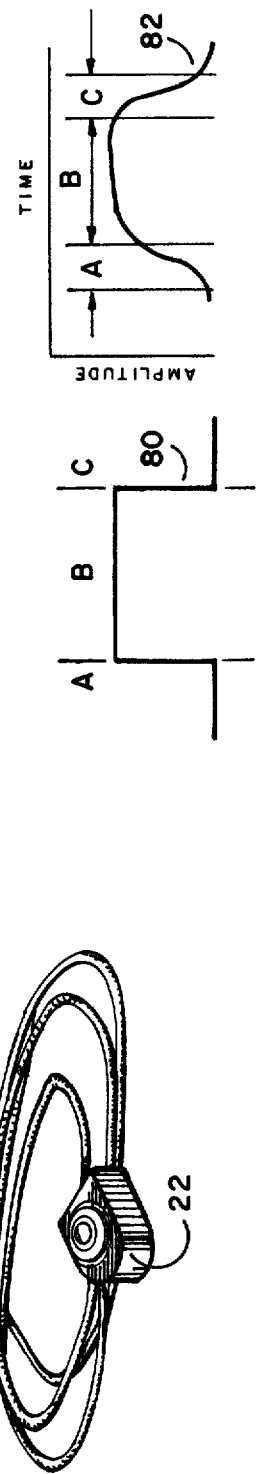
FIG. 3 is a graphic representation of wave functions capable of being produced by the circuitry of the present invention as depicted in FIG. 2.

To combat the attendant production of pain associated with the square wave, a gradual increase, surge, or rise of the wave to its amplitude is accomplished by the interposition of capacitor 90 in association with collector 66 of transistor 68 and appropriate output stage circuitry. Capacitor 90, which is charged through resistor 64 and gradually discharged, is in the range of thirty microfarads and will cause the rise, surge and decay of the output wave to be gradual and extended in time as determined by the value of the capacitor. The wave function thus produced is illustrated in FIG. 3 and designated 82.

Since the rise and decay time are known and since the total pulse time is predetermined, it is possible to control therefore the time of full amplitude by adjusting the aforementioned potentiometer 38. Since the build up of the wave to full energy or amplitude is gradual, there is less of a shock to the body.

The resultant wave actuation voltage is fed to output stage circuitry 100 which is a tuning and an amplifier circuit. The amplifier primarily consists of transistor 102 which is driven by the amplification circuit 44 output. Transistor 102 is overrated so that it may withstand potential reflected waves and standing waves from the output probe which produces the waves.

Tuning of the output stage to coaxial cable which can be a 72 inch RG174U cable or equivalent output is accomplished by a conventional pi circuit.

It should be noted that the foregoing embodiment is merely illustrative of a preferred embodiment for the present invention and it is recognized that various changes, modifications and variations may be made without departing from the spirit and scope of the following claims.

I claim:

1. An improved epilation apparatus having a circuit for producing for a predetermined time a high frequency wave output at a probe, such apparatus comprising:

(1) means for producing a pulse having a duration of a predetermined time;

(2) a high frequency oscillator operating in the range of approximately 13 MHz;

(3) electronic switching means, having first and second inputs, with the first input connected to the high frequency oscillator and the second input connected to the pulse producing means, in such fashion as to produce a high frequency output over the approximate duration of a pulse present at the second input, such electronic switching means including (a) a first transistor, connected as an amplifier having an input between its base and its emitter and an output between its collector and its emitter, and also connected so that its input, being the first input of the electronic switching means, is connected to the high frequency oscillator output;
(b) a resistor, connected at one end to the emitter of the first transistor;
(c) a second transistor, connected as an amplifier having an input between its base and its emitter and an output between its collector and its emitter; and also connected (i) so that its collector is connected to the other end of the resistor so as to place the output of the second transistor in series with the output of the first transistor, the current through this series combination providing the high frequency output of the electronic switching means, and (ii) so that the second transistor's input, being the second input of the electronic switching means, receives the output from the pulse-producing means;
(d) a capacitor, connected between the collector of the second transistor and its emitter, such capacitor being charged and discharged through the series combination of the outputs of the first and second transistors in such a way that the amplitude of the high frequency output of the electronic switching means gradually rises and decays over the approximate duration of a pulse present at the second transistor's input;
(4) a transistor power output stage having an input connected to the high frequency output of the electronic switching means and an output; and
(5) an epilation needle probe connected to the output of the transistor power output stage.

* * * * *